United States Patent [19]
Hergenrother et al.

[11] Patent Number: 5,750,206
[45] Date of Patent: May 12, 1998

[54] METHOD OF PRETREATING METAL SURFACES FOR SUBSEQUENT POLYMER COATING

[75] Inventors: Robert Hergenrother, Fremont; Uriel Hiram Chee, San Carlos; Laurent Schaller, Los Altos, all of Calif.

[73] Assignee: Target Therapeutics, Inc., Fremont, Calif.

[21] Appl. No.: 429,599

[22] Filed: Apr. 27, 1995

Related U.S. Application Data

[62] Division of Ser. No. 97,458, Jul. 27, 1993, Pat. No. 5,388,343.

[51] Int. Cl.$^6$ ............................................. C08J 7/18
[52] U.S. Cl. .................... 427/490; 427/409; 427/488; 427/498; 427/535; 427/569; 427/582
[58] Field of Search ........................ 427/488, 490, 427/498, 535, 569, 582, 409

[56] References Cited

U.S. PATENT DOCUMENTS

| | | | |
|---|---|---|---|
| 3,397,132 | 8/1968 | Wolinski et al. | 204/165 |
| 4,100,309 | 7/1978 | Micklus et al. | 427/2.28 |
| 4,459,317 | 6/1984 | Lambert | 427/2.25 |
| 4,499,124 | 2/1985 | Pusineri et al. | 427/385.5 |
| 4,524,089 | 6/1985 | Haque et al. | 427/38 |
| 4,589,873 | 5/1986 | Schwartz et al. | 208/410 |
| 4,689,111 | 8/1987 | Chan et al. | 156/643 |
| 4,705,709 | 11/1987 | Valiancourt | 428/36.91 |
| 4,722,906 | 2/1988 | Guire | 436/501 |
| 4,810,543 | 3/1989 | Gould | 428/35.7 |
| 4,934,380 | 6/1990 | de Toledo | 128/772 |
| 4,973,493 | 11/1990 | Guire | 427/2.24 |
| 4,977,901 | 12/1990 | Ofstead | 128/772 |
| 4,979,959 | 12/1990 | Guire | 623/66 |
| 5,002,582 | 3/1991 | Guire et al. | 623/66 |
| 5,055,316 | 10/1991 | Hoffman et al. | 530/359 |
| 5,095,915 | 3/1992 | Engelson | 128/772 |
| 5,112,457 | 5/1992 | Marchant | 204/165 |
| 5,128,170 | 7/1992 | Matsuda et al. | 427/2.24 |
| 5,129,890 | 7/1992 | Bates et al. | 604/281 |
| 5,135,516 | 8/1992 | Sahatjian et al. | 604/265 |
| 5,190,529 | 3/1993 | McCrory et al. | 604/175 |
| 5,242,389 | 9/1993 | Schrader et al. | 604/54 |
| 5,272,012 | 12/1993 | Opolski | 428/423.1 |
| 5,284,543 | 2/1994 | Kusano et al. | 156/272.6 |

FOREIGN PATENT DOCUMENTS

WO89/11919  12/1989  WIPO.

OTHER PUBLICATIONS

Bio–Metric Systems Technical Bulletin entitled "BioCoat™ Medical Device Coating Technology" Bio–Metric Systems, Inc., 9924 W. 74th St., Eden Prairie, MN, 55344, 24 pages total (No date avail.).

Bell, A.T., "Fundamentals of plasma polymerization" *Symposuim on Plasma Chemistry of Polymers* (1976) Marcel Dekker, Inc., New York. pp. 1–13. (No month avail.).

(List continued on next page.)

*Primary Examiner*—Bernard Pianalto
*Attorney, Agent, or Firm*—Morrison & Foerster

[57] ABSTRACT

This invention relates to a new technique for preparing metal devices such as guidewires for the subsequent attachment of hydrophilic coatings. The invention also relates to guidewires and other devices made according to that method.

In one embodiment of the method of this invention, a hydrocarbon residue undercoat is applied to a metal guidewire core by plasma deposition. A photoactive hydrophilic polymer is then deposited on the hydrocarbon residue coating and activated by ultraviolet light. The hydrocarbon residue coating acts as a tie layer between the hydrophilic polymer and the metal guidewire core apparently by providing C—C bonds for the covalent linking of the coating material to the tie layer. The resulting article of this invention is a guidewire having the maneuverability of a metal guidewire and the biocompatibility of a lubricious, hydrophilic polymer.

12 Claims, 1 Drawing Sheet

OTHER PUBLICATIONS

Bruck, S.D. "The behavior of three different types of materials in vitro and in the dynamic physiological environment: Review and analyses of critical parameters" *Third International Congress of Biorheology* (Aug. 28–Sep. 1, 1978), La Jolla (San Diego), CA, pp. 31–34.

Coury, A.J. et al., "Plastics Technology/Recent developments in hydrophilic polymers" *MD&DI* (1984) pp. 28–30. (No month avail.).

Dynes, P.J. et al., "Plasma polymerization on metals" *Symposium on Plasma Chemistry of Polymers* (1976) Marcel Dekker, Inc., NY, pp. 167–189. (No month avail.).

Evangelista, R.A. et al., "Coating of two polyether–plyurethanes and polyethylene with a heparin–poly–(vinyl alcohol) hydrogel" *Biomaterials* (1986) 7:206–211. (No month avail.).

Feng, X–D., "Some advances in synthetic biomedical polymers" *Polymer Journal* (1985) 17:189–200. (No month avail.).

Francis, D. et al., "Engineering thermopastics in reusable medical applications" *Materials Engineering* (1988). (No month avail.).

Hoffman, A.S., "Letter to the Editor: A general classification scheme for 'hydrophillic' and 'hydrophobic' biometerial surfaces" *Journal of Biomedical Materials Research* (1986) 20:ix–xi. (No month avail.).

Horak, D. et al., "Hydrogels in endovascular embolization. I. Spherical particles of poly (2–hydroxyethyl methacrylate) and their medico–biological properties" *Biomaterials* (1986) 7:188–192. (No month avail.).

Inagaki, N. et al., "Adhesion of glow discharge polymers to metals and polymers" *Journal of Applied Polymer Science* (1981) 26:3333–3341. (No month avail.).

Ito, Y. et al., "Synthesis and antithrombogenicity of anionic polyurethanes and heparin–bound polyurethanes" *Journal of Biomedical Research* (1986) 20:1157–1177. (No month avail.).

Jansen, B. et al., "Modification of polyetherurethane for biomedical application by radiation induced grafting. II. Water sorption, surface properties, and protein adsorption of grafted films" *Journal of Biomedical Research* (1984) 18:655–669. (No month avail.).

Klomp, G. F. et al., "Macroporous hydrogel membranes for a hybrid artificial pancreas. II. Biocompatibility." *Journal of Biomedical Materials Research*(1983) 17:865–871. (No month avail.).

Marchant, R. E. et al., "A hydrophilic plasma polymerized film composite with potential application as an interface for biomaterials" *Journal of Biomedical Materials Research* (1990) 24:1521–1537. (No month avail.).

Marchant, R. E. et al., "Preparation and characterization of plasma–polymerized N–vinyl–2–pyrrolidone films" *Journal of Polymer Science: Part A: Polymer Chemistry* (1989) 27:881–895. (No month avail.).

Miyama, H. et al. "Antithrombogenic heparinized polyacrylonitrile copolymer" *Journal of Biomedical Materials Research* (1986) 20:895–901. (No month avail.).

Peppas, N. A. et al., "The structure of highly crosslinked poly(2–hydroxyethyl methacrylate) hydrogels" *Journal of Biomedical Materials Research* (1985) 19:397–411. (No month avail.).

Pinchuk, L. et al., "The interaction of urea with the generic class of poly(2–hydroxyethyl methacrylate) hydrogels" *Journal of Biomedical Materials Research* (1984) 18:671–684. (No month avail.).

Ronel, S. H. et al., "Macroporous hydrogel membranes for a hybrid artificial pancreas. I. Synthesis and chamber fabrication." *Journal of Biomedical Materials Research* (1983) 17:855–864. (No month avail.).

Seifert, L. M. et al., "Evaluation of in vivo adsorption of blood elements onto hydrogel–coated silicone rubber by scanning electron microscopy and fourier transform infrared spectroscopy" *Journal of Biomedical Materials Research* (1985) 19:1043–1071. (No month avail.).

Takahara, A. et al., "Effect of aggression state of hard segment in segmented poly(urethaneureas) on their fatigue behavior after interaction with blood components" *Journal of Biomedical Materials Research* (1985) 19:13–34. (No month avail.).

Ward, R. S., "Plastics Technology/Softenable, shape–memory thermoplastics for biomedical use" *MD&DI* (1985) pp. 84–32. (No month avail.).

Technical Bulletin/Photolink surface modification for medical devises *Bio–Metric Systems, Inc.* (May 1991).

METHOD OF PRETREATING METAL SURFACES FOR SUBSEQUENT POLYMER COATING

This application is a division of application Ser. No. 08/097,458 filed Jul. 27, 1993 U.S. Pat. No. 5,388,343.

FIELD OF THE INVENTION

This invention relates generally to a method for preparing a surface for subsequent attachment of a coating and, in particular, to a method for preparing a metal surface for subsequent covalent linking to a polymer coating. This invention also relates to articles such as medical devices made according to this method.

BACKGROUND OF THE INVENTION

The surface of an object may be coated with a polymer to protect the surface or to provide the surface with properties of the polymer coating. For example, coatings of synthetic polymers and natural biomolecules are applied to medical devices for a variety of reasons. In the case of catheters and guidewires, it is desirable to add a coating with a low coefficient of friction in the presence of water and a low tendency to form clots (thromboembolisms) in the presence of blood.

As discussed in U.S. Pat. No. 5,002,582, the disclosure of which is incorporated herein by reference, polymer molecules may be provided with latent reactive groups covalently bonded to them such that when the molecules are brought into bonding proximity with a surface (such as on a medical device), the latent reactive groups can be energized to form, via free active species generation, covalent bonds between these molecules and the surface. The latent reactive groups generate active species such as free radicals, nitrenes, carbenes, and excited states of ketones upon absorption of external electromagnetic or kinetic (thermal) energy.

The '582 patent describes a number of suitable latent reactive groups and some methods of applying polymers and other coatings to a surface using the latent reactive groups. Under one method, a solution containing a latent reactive molecule (e.g., a molecule having a latent reactive group) is applied to the surface. Thereafter, the desired polymer is brought into contact with, and is covalently bonded to, the latent reactive molecule, as to a reactive group different from the latent reactive group, to form a photocrosslinkable polymer system. The latent reactive groups may then be activated to cause the photocrosslinkable polymer system to covalently bond to the surface.

Under another method disclosed in the '582 patent, the surface is first coated with a solution of the molecules bearing latent reactive groups. UV light is applied to cause the molecules to covalently bond, through the latent reactive groups, to the surface. A solution containing the desired polymer is then applied to the surface, and the polymer bonds covalently to the photoactively treated surface. Further details of photoactive and thermally active covalent attachment of polymers may be found in U.S. Pat. Nos. 4,722,906; 4,973,493; and 4,979,959. The disclosures of these patents are incorporated herein by reference.

Bio-Metric Systems, Inc., markets a photoactive biocompatible coating technique under the trademark BioCoat. This technique first combines a photoactive binder and the desired coating material, such as a hydrophilic polymer, to create a photocrosslinkable polymer system. A solution of the photocrosslinkable polymer system is then applied to the medical device. The coating is dried, and the binder is cured with UV light to covalently bond the hydrophilic photocrosslinkable polymer system to the surface of the device.

Catheter guidewires are one example of the kind of medical device typically coated with a biocompatible material. In order to facilitate insertion of the guidewire into a patient and to minimize the threat of thromboembolisms, the metal core must be surrounded by a lubricious hydrophilic polymer coating. The coatings of prior art guidewires, however, are inadequate, for the reasons stated below.

The BioCoat process and the processes disclosed in U.S. Pat. Nos. 4,722,906; 4,973,493; 4,979,959; and 5,002,582 have not been used successfully to coat metal devices such as guidewires with hydrophilic polymers (despite suggestions to the contrary in those references) without first preparing or pretreating the surface of the devices, particularly when the coated metal devices are used in an aqueous environment. Two possible pretreatments have been proposed. Under one approach, the guidewire is prepared for subsequent coating by shrink-wrapping a polyethylene sleeve around the guidewire. The photocrosslinkable hydrophilic polymer system is then applied, dried and cured as described above. In another possible pretreatment method, the guidewire is prepared for subsequent coating by dipping the guidewire in a silane undercoat solution, then drying. The photocrosslinkable hydrophilic polymer system is then applied to the silane undercoating.

Other prior art methods of applying biocompatible coatings to metal devices use preparation methods that fall into the same two categories as the photoactive binder approaches mentioned above: (1) wet undercoat pretreatment methods and (2) solid sleeve undercoat pretreatment methods. For example, a wet undercoat method of applying a biocompatible, hydrophilic coating to a catheter or guidewire is disclosed in U.S. Pat. No. 5,135,516. The coating described in the '516 patent comprises an isocyanate primer, a lubricious binding component and an antithrombogenic component. The binding component is a hydrophilic, water-swellable, acid-containing polymer with quaternary ammonium cations bonded into the polymer layer. In one disclosed application method, a stainless steel guidewire is coated first with a primer solution of a 1% polyisocyanate in methylethylketone, then dried for 30 minutes. A topcoat of 1% poly(acrylic acid) and 0.5% of MYRJ 53 (nonionic surfactant) in dimethylformamide is then applied and dried for another 30 minutes. The resulting hydrophilic surface is then dipped first in a benzalkonium chloride solution, then dried and dipped in a heparin salt solution to complete the process.

U.S. Pat. No. 5,129,890 describes a solid sleeve pretreatment method for coating a metal guidewire with a lubricious coating. The guidewire coating method disclosed in the '890 patent interposes a polyurethane sleeve between the hydrophilic coating and the guidewire. The sleeve provides an attachment base for the hydrophilic coating.

SUMMARY OF THE INVENTION

One drawback of prior art wet undercoat preparation methods of coating metal devices with biocompatible hydrophilic polymers is the time needed to apply and dry the undercoat before the application of the hydrophilic polymer itself. Another drawback of prior wet undercoat pretreatment methods is the difficulty of obtaining an even layer of the wet undercoat. Any irregularities in the thickness of the undercoat will affect the quality of the hydrophilic outer coating.

The use of wet treatment methods is additionally becoming increasingly more of an environmental concern. The materials used in cleaning, coating, and rinsing the medical devices are now often difficult, or at least very expensive, to dispose of.

Another drawback of wet undercoating techniques is the drying time required for each coating layer. Longer manufacturing times translate into higher manufacturing costs and can make the resulting article prohibitively expensive.

A drawback of the solid sleeve undercoat approach is the thickness of the resulting product. The combined thicknesses of the sleeve and hydrophilic coating makes the guidewire less maneuverable and harder to use. If, on the other hand, the guidewire diameter is made thinner in order to accommodate the additional thickness of the sleeve, the guidewire will be less stiff and harder to control. What is needed, therefore, is a method for preparing metal devices such as guidewires for subsequent application of hydrophilic coatings that avoids these and other problems.

This invention relates to a new technique for preparing metal devices such as guidewires for the subsequent attachment of hydrophilic coatings. The invention also relates to guidewires and other devices made according to that method.

In one embodiment of the method of this invention, a hydrocarbon residue undercoat is applied to a metal guidewire core by plasma deposition. A photoactive hydrophilic polymer is then deposited on the hydrocarbon residue coating and activated by ultraviolet light. The hydrocarbon residue coating acts as a tie-layer between the hydrophilic polymer and the metal guidewire core by providing C—C bonds for the covalent linking of the coating material to the tie-layer. The resulting article of this invention is a guidewire having the maneuverability of a completely metal guidewire and the biocompatibility of a lubricious, hydrophilic polymer.

The invention is described in more detail below with reference to the drawings.

DESCRIPTION OF THE INVENTION

This invention is a method for preparing or pretreating guidewires and other metal devices to receive a subsequent coating of a polymer, preferably a polymer which is lubricious, biocompatible, and hydrophilic. The preferred method will be discussed in relation to a metal guidewire. A metal guidewire core is placed in a plasma chamber and cleaned with an oxygen plasma etch. The guidewire core is then exposed to a hydrocarbon plasma to deposit a plasma-polymerized tie layer on the guidewire core to complete the pretreatment. The hydrocarbon plasma may comprise a lower molecular weight (or gaseous) alkanes such as methane, ethane, propane, isobutane, butane or the like; lower molecular weight alkenes such as ethene, propene, isobutene, butene or the like or; gaseous fluorocarbons such as tetrafluoromethane, trichlorofluoromethane, dichlorodifluoromethane, trifluorochloromethane, tetrafluoroethylene, trichlorofluoroethylene, dichlorodifluoroethylene, trifluorochloroethylene and other such materials. Mixtures of these materials are also acceptable. The tie layer apparently provides C—C bonds for subsequent covalent bonding to the outer hydrophilic polymer coating. Preferred flow rates for the hydrocarbon into the plasma chamber are in the range of 500 c.c./min. to 2000 c.c./min. and the residence time of the guidewire in the chamber is in the range of 1–20 minutes, depending on the chosen hydrocarbon and the plasma chamber operating parameters. Power settings for the plasma chamber are preferably in the range of 200 W to 1500 W.

The pretreated guidewire may be coated by a polymer in a manner known in the prior art. For example, in one embodiment of the preferred apparatus of this invention, the pretreated guidewire is dipped in a solution of a photoactive hydrophilic polymer system, i.e., a latently photoreactive binder group covalently bonded to a hydrophilic polymer. After drying, the coated guidewire is cured by exposing it to UV light. The UV light activates the latently reactive group in the photoactive polymer system to form covalent bonds with crosslinked C—C bonds in the hydrocarbon residue tie layer. The dipping and curing steps are preferably repeated often enough, typically twice, to achieve the appropriate thickness of the hydrophilic coating layer.

Figure 1:
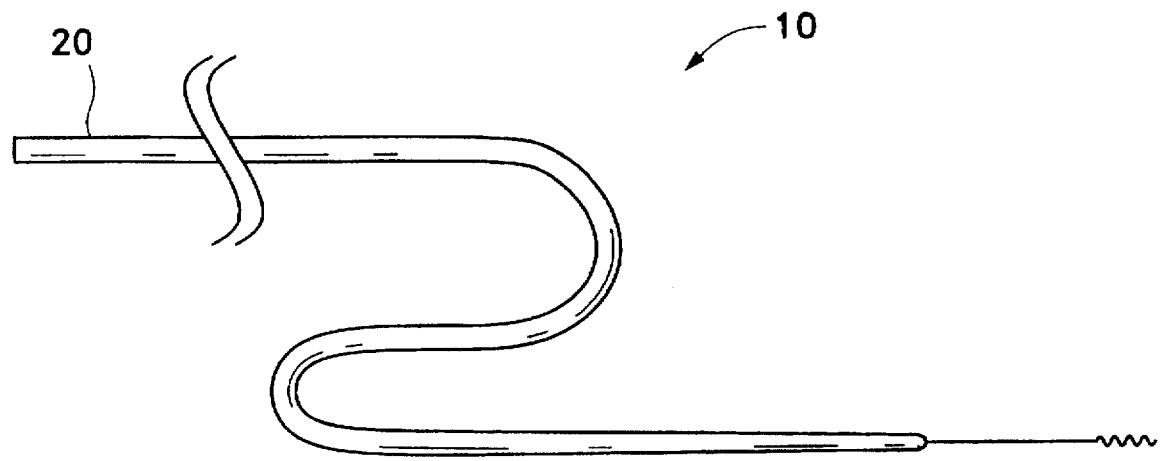
FIG. 1 is a plan view of a guidewire made according to the method of this invention.
Figure 2:
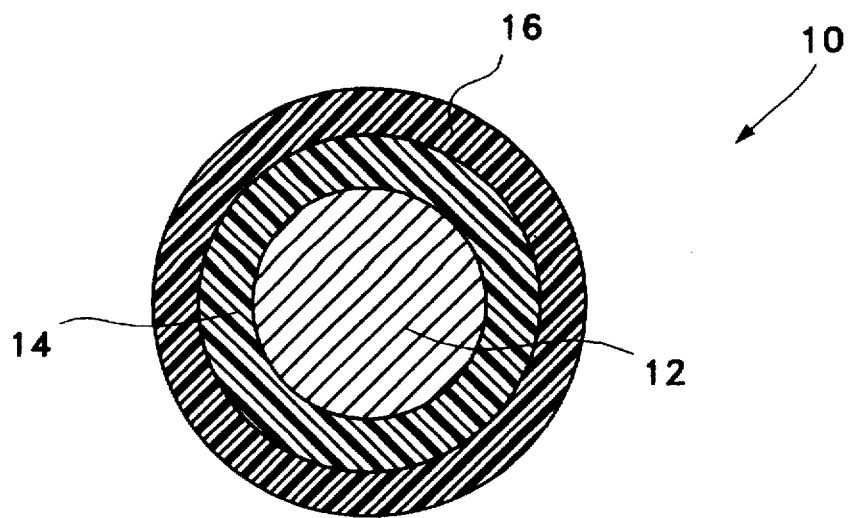
FIG. 2 is a cross-sectional drawing of a portion of the guidewire of FIG. 1.

One preferred embodiment of a product made according to this invention is shown in FIGS. 1 and 2. A metal guidewire 10 is coated over most of its length by a lubricious hydrophilic polymer. The guidewire has an uncoated region 20 at its proximal end to provide the user with a gripping surface.

FIG. 2 schematically depicts a cross-section of the guidewire of FIG. 1. The dimensions have been exaggerated to better show the individual elements of the invention. Guidewire 10 has a metal core 12, preferably 0.010 to 0.0251" thick stainless steel or nitinol. The exterior surface of guidewire 10 is a biocompatible coating 16 of a polyacrylamide/polyvinylpyrrolidone mixture bonded to a photoactive binding agent. The lubricious and hydrophilic character of coating 16 facilitates insertion of the guidewire into a patient and helps reduce the incidence of thromboemboli while the guidewire is within the patient's body. In the preferred embodiment, coating 16 is made from a mixture of Bio-Metric Systems PA03 and PV01 binding systems according to Examples 1–4 below.

A tie layer 14 of plasma produced hydrocarbon residue having a thickness on the order of 10 Å thick is disposed between core 12 and coating 16. This process typically produces layers of hydrocarbon residue less than about 1000 Å in thickness, and more typically less than about 100 Å. Tie layer 14 effectively bonds layer 16 to metal core 12 while adding very little additional bulk to the guidewire. Guidewires made according to this invention therefore avoid the size and maneuverability problems of prior art guidewires.

Other materials may be substituted for the materials of the preferred embodiment without departing from the invention. For example, the guidewire core may be made from stainless steel, nitinol, or platinum with a diameter in the range of 0.010"–0.038".

The photoactive hydrophilic polymer system of this preferred embodiment is a mixture of Bio-Metric Systems PA03 polyacrylamide/binder system and Bio-Metric Systems PA01 polyvinylpyrrolidone system. The polyacrylamide system provides lubricity, and the polyvinylpyrrolidone system provides both lubricity and binding for durability. The exact proportions of the two systems may be varied to suit the application. As an alternative, however, the hydrophilic biocompatible coating may be polyacrylamide alone, polyvinylpyrrolidone alone, polyethylene oxide, or any suitable coating known in the art. In addition, a coating of heparin, albumin or other proteins may deposited over the hydrophilic coating in a manner known in the art to provide additional biocompatibility features.

The guidewire or other device may be cleaned by using an argon plasma etch in place of the oxygen plasma etch. The thickness of the plasma-polymerized tie layer may also vary without departing from the scope of this invention.

The following examples are further illustrative of the articles and methods of this invention. The invention is not limited to these examples.

EXAMPLE 1

A 0.014" diameter stainless tapered steel guidewire was placed in a Plasma Etch MK II plasma chamber and cleaned with an oxygen plasma for 2 minutes. Ethane flowing at a rate of 700 c.c./min. was admitted into the chamber, and the chamber was operated at a power setting of 800 W for 5 minutes to plasma treat the ethane into a hydrocarbon residue on the surface of the wire. All but approximately six inches of the wire was dipped in a polyvinylpyrrolidone/ polyacrylamide (PVP/PA) photocrosslinkable solution consisting essentially a mixture of 50% BSI PV01 and 50% BSI PA03. The coated guidewire was then dried and exposed to an ultraviolet light (325 nm.) for 8 seconds. The dipping, drying and exposing steps were repeated twice. When wetted, the resulting wire felt lubricious and required less force to pull through an 0.018" ID catheter than an uncoated wire.

EXAMPLE 2

A 0.014" diameter stainless tapered steel guidewire was placed in a Plasma Etch MK II plasma chamber and cleaned with an oxygen plasma for 2 minutes. Ethane flowing at a rate of 1200 c.c./min. was admitted into the chamber, and the chamber operated at a power setting of 1000W for 5 minutes to plasma treat the ethane into a hydrocarbonaceous rseidue on the su***rface of the wire. All but approximately six inches of the wire was dipped in a polyvinylpyrrolidone/ polyacrylamide (PVP/PA) photocrosslinkable solution of a mixture of 33% BSI PV01 and 67% BSI PA03. The coated guidewire was then dried and exposed to an ultraviolet light (325 nm.) for 8 seconds. The dipping, drying, and exposing steps were repeated. When wetted, the resulting wire felt lubricious and required less force to pull through an 0.018" ID catheter than an uncoated wire.

EXAMPLE 3

A 0.016" diameter nitinol guidewire was placed in a Plasma Etch MK II plasma chamber and cleaned with an oxygen plasma for 10 minutes. Methane flowing at a rate of 2000 c.c./min. was admitted into the chamber, and the chamber operated at a power setting of 400 W for 2 minutes to deposit a hydrocarbonaceous residue onto the surface of the wire. All but approximately six inches of the wire was dipped in a polyvinylpyrrolidone/polyacrylamide (PVP/PA) photocrosslinkable solution of a mixture of 67% BSI PV01 and 33% BSI PA03. The coated guidewire was then dried and exposed to an ultraviolet light (325 nm.) for 8 seconds. The dipping, drying, and exposing steps were repeated twice. When wetted, the resulting wire felt lubricious and required less force to pull through an 0.018" ID catheter than an uncoated wire.

EXAMPLE 4

A 0.016" diameter nitinol guidewire was placed in a Plasma Etch MK II plasma chamber and cleaned with an oxygen plasma for 10 minutes. Methane flowing at a rate of 1500 c.c./min. was admitted into the chamber, and the chamber was operated at a power setting of 600 W for 5 minutes to plasma treat the methane into a hydrocarbonaceous on the surface of the wire. All but approximately six inches of the wire was dipped in a polyvinylpyrrolidone/ polyacrylamide (PVP/PA) photocrosslinkable solution consisting essentially a mixture of 50% BSI PV01 and 50% BSI PA03. The coated guidewire was then dried and exposed to an ultraviolet light (325 nm.) for 8 seconds. The dipping, drying, and exposing steps were repeated. When wetted, the resulting wire felt lubricious and required less force to pull through an 0.018" ID catheter than an uncoated wire.

EXAMPLE 5

A 0.016" diameter nitinol guidewire was placed in a Plasma Etch MK II plasma chamber and cleaned with an oxygen plasma for 10 minutes. Ethane flowing at a rate of 900 c.c./min. was admitted into the chamber, and the chamber was operated at a power setting of 600 W for 10 minutes to deposit a hydrocarbon residue onto the surface of the wire. All but approximately six inches of the wire was dipped in a polyvinylpyrrolidone/polyacrylamide (PVP/PA) photocrosslinkable solution of a mixture of 33% BSI PV01 and 67% BSI PA03. The coated guidewire was then dried and exposed to an ultraviolet light (325 nm.) for 8 seconds. The dipping, drying, and exposing steps were repeated twice. When wetted, the resulting wire felt lubricious and required less force to pull through an 0.018" ID catheter than an uncoated wire.

EXAMPLE 6

An 0.014" diameter stainless steel wire was placed in an Advanced Plasma Systems plasma chamber and cleaned with an oxygen plasma. Tetrafluoroethylene flowing at a rate of 1000 c.c./min. was admitted into the chamber, and the chamber was operated at a power setting of 1000 W for 10 minutes to deposit a fluorocarbon residue onto the surface of the wire. All but approximately six inches of the wire was dipped in a polyvinylpyrrolidone/polyacrylamide (PVP/PA) photocrosslinkable solution of a mixture of 67% BSI PV01 and 33% BSI PA03. The coated guidewire was then dried and exposed to an ultraviolet light (325 nm.) for 8 seconds. The dipping, drying, and exposing steps were repeated twice. When wetted, the resulting wire felt lubricious and required less force to pull through an 0.018" ID catheter than an uncoated wire.

EXAMPLE 7

An 0.016" diameter stainless steel wire was placed in an Advanced Plasma Systems plasma chamber and cleaned with an oxygen plasma. Tetrafluoromethane flowing at a rate of 1500 c.c./min. was admitted into the chamber, and the chamber was operated at a power setting of 1200 W for 10 minutes to deposit a fluorocarbon residue onto the surface of the wire. All but approximately six inches of the wire was dipped in a polyvinylpyrrolidone-polyacrylamide (PVP/PA) photocrosslinkable solution of a mixture of 50% BSI PV01 and 50% BSI PA03. The coated guidewire was then dried and exposed to an ultraviolet light (325 nm.) for 8 seconds. The dipping, drying, and exposing steps were repeated twice. When wetted, the resulting wire felt lubricious and required less force to pull through an 0.018" ID catheter than an uncoated wire.

We claim as our invention:

1. A method of coating a metal surface with a polymer comprising the following steps:

exposing a metal surface to a hydrocarbon plasma to deposit a hydrocarbon residue on the metal surface, depositing a photocrosslinkable system on the hydrocarbon residue, the photocrosslinkable system comprising molecules of a polymer and a chemical linking moiety possessing a photochemically reactive group capable upon activation of covalently bonding to the hydrocarbon residue; and activating the photochemically reactive group of the chemical linking moiety to cause the photochemically reactive group to covalently bind to the hydrocarbon residue.

2. The method of claim 1 in which the plasma hydrocarbon comprises at least one member selected from low molecular weight alkanes, alkenes, and fluorocarbons.

3. The method of claim 2 in which the plasma hydrocarbon is methane.

4. The method of claim 1 in which the polymer is a hydrophilic polymer.

5. The method of claim 4 in which the hydrophilic polymer comprises polyvinylpyrrolidone.

6. The method of claim 5 in which the hydrophilic polymer further comprises polyacrylamide.

7. A method of coating a metal surface with a polymer comprising the following steps:

depositing a hydrocarbon residue on a metal surface by exposing the metal surface to a hydrocarbon plasma; and covalently bonding a polymer to the hydrocarbon residue.

8. The method of claim 7 in which the hydrocarbon plasma comprises at least one member selected from low molecular weight alkanes, alkenes, and fluorocarbons.

9. The method of claim 8 in which the hydrocarbon plasma is methane.

10. The method of claim 8 in which the polymer is a hydrophilic polymer.

11. The method of claim 10 in which the hydrophilic polymer comprises polyvinylpyrrolidone.

12. The method of claim 11 in which the hydrophilic polymer further comprises polyacrylamide.

* * * * *

UNITED STATES PATENT AND TRADEMARK OFFICE
CERTIFICATE OF CORRECTION

PATENT NO. : 5,750,206
DATED : May 12, 1998
INVENTOR(S) : Hergenrother et al.

It is certified that error appears in the above-identified patent and that said Letters Patent is hereby corrected as shown below:

On the title page,

[56] References Cited, Column 1, U.S. Patent Documents, U.S. 4,374,694, 1/1983 should be listed.
Column 2, Other Publications, line 14, "*Symposuim*" should be --*Symposium*--.

Page 2, Other Publications, Column 1, line 12, "-plyure-" should be --polyure- --; line 19, "thermopastics" should be --thermoplastics--; line 23, "hydrophillic" should be --hydrophilic--, line 35, "*Biomedical Research*" should be --*Biomedical Materials Research*--; line 40, "*Biomedical Research*" should be --*Biomedical Materials Research*--.
Column 2, line 33, "aggression" should be --aggregation--.

Column 5, line 22, "essentially a" should be --essentially of a--; line 36, "rseidue" should be --residue--; line 37, "su\*\*\*rface" should be --surface--.

Column 8, Claim 7, line 6, "the" should be --a--; line 8, "a" should be --the--.

Signed and Sealed this

Twentieth Day of July, 1999

Attest:

Q. TODD DICKINSON

*Attesting Officer*  Acting Commissioner of Patents and Trademarks